United States Patent [19]

Piazza, Jr. et al.

[11] Patent Number: 5,932,458

[45] Date of Patent: Aug. 3, 1999

[54] METHOD OF RAPID FAT AND OIL SPLITTING USING A LIPASE CATALYST FOUND IN SEEDS

[75] Inventors: George J. Piazza, Jr., Rydal; Michael J. Haas, Wyndmoor, both of Pa.

[73] Assignee: The United States of America as represented by the Secretary of Agriculture, Washington, D.C.

[21] Appl. No.: 07/855,805

[22] Filed: Mar. 23, 1992

[51] Int. Cl.⁶ ............................. C12N 11/10; C12N 11/12
[52] U.S. Cl. .................... 435/174; 435/134; 435/177; 435/178; 435/198
[58] Field of Search ...................... 435/174, 177, 435/178, 198, 134

[56] References Cited

U.S. PATENT DOCUMENTS

| | | | |
|---|---|---|---|
| 3,713,980 | 1/1973 | Balsam et al. ............................. | 435/99 |
| 4,011,169 | 3/1977 | Diehl et al. | |
| 5,089,403 | 2/1992 | Hammond et al. ...................... | 435/134 |
| 5,089,404 | 2/1992 | Matsumoto et al. .................... | 435/134 |

OTHER PUBLICATIONS

Lee et al., *JAOCS*, vol. 67, No. 11 (Nov. 1990), pp. 761–765.
Piazza, et al*JAOCS*, vol. 66, No. 4 (Apr. 1989), p. 489.
Bilyk et al., "Lipase Catalyzed Tallow Hydrolysis in Organic Solvents,"Abstract #022, *Inform* (Apr. 1990).
Piazza, *Biotechnology Letters*, vol. 13, No. 3, pp. 173–178 (1991).

*Primary Examiner*—Leon B. Lankford, Jr.
*Attorney, Agent, or Firm*—M. Howard Silverstein; Joseph A. Lipovsky; John D. Fado

[57] ABSTRACT

A method of producing fatty acids and glycerol from oleaginous materials utilizing comminuted seeds as an immobilized lipase catalyst. The comminuted lipase-containing seeds are combined with an oleaginous material, an organic solvent and water with the resultant heterogenous mixture being agitated under non-energy intensive conditions to provide free fatty acids and glycerol. The lipase catalyst may be recovered and recycled.

8 Claims, 3 Drawing Sheets

METHOD OF RAPID FAT AND OIL SPLITTING USING A LIPASE CATALYST FOUND IN SEEDS

BACKGROUND OF THE INVENTION

1. Field of the Invention

The present invention relates to an efficient and inexpensive method of rapidly hydrolyzing oleaginous materials of all types into their constituent fatty acids and glycerol. This method will increase the production of fatty acids while reducing costs. The present invention also relates to an inherently immobilized lipase catalyst created from seeds which can be used to hydrolyze oleaginous materials with reduced reaction times despite use of modest temperatures.

2. Description of Related Art and Information

Fatty acids are important industrial chemicals used in the production of alkyd resins, dimer acids and dicarboxylic acids. The fatty acid industry has continuously attempted to increase free fatty acid production by searching for new methods of fat and oil hydrolysis. At the present time, in the fatty acid industry, hydrolysis of fats and oils is accomplished by a high-temperature steam treatment method known as the Colgate-Emery Steam Hydrolysis Process [Brady, C., L. Metcalfek, D. Slaboszewski, and D. Frank, JAOCS, 65:917–921 (1988)]. This process operates with super-heated steam at 250° C. and 50 atm. A two hour reaction results in a 97% yield of fatty acids. This high-temperature process is energy intensive, and causes extensive degradation of the produced fatty acids. Purification of the fatty acid product by means such as distillation is required prior to its recovery. In order to avoid degradation problems, some sectors of industry create fatty acids from vegetable oils by splitting such oils with a base followed by acidulation. This procedure does not, however, achieve complete splitting.

The use of enzymes to split fats is well known in the prior art. In 1948, A. W. Ralston reported that in 1890, Green and Sigmund, working independently, established the presence of a fat-splitting enzyme in castor beans, [Ralston, A. W., "Fatty Acids and Their Derivatives," John Wiley & Sons, Inc., p. 275 (1948)]. These enzymes, known as lipases, function at an oil-water interface to hydrolyze fats and oils to fatty acids and glycerol. Many investigators have studied the enzymatic reaction and have encountered difficulty isolating the fatty acids from the heavy emulsion which is formed, [Sonntag, N. O. V., *Fat Splitting and Glycerol Recovery in Fatty Acids in Industry*, edited by R. W. Johnson and E. Fritz, Marcel Dekker, Inc., New York, N.Y. (1989)].

Hydrolysis of olive oil using *Candida rugosa* lipase has been reported, [Linfield, W. M., D. J. O'Brien, S. Serota and R. A. Barauskas, *J. Am. Oil Chem. Soc.*, 61:1067–1071, (1984)]. However, successful hydrolysis required prior treatment of the oil with bleaching earth.

Lipase-catalyzed hydrolysis of soybean oil has been reported. However, nearly complete lipolysis required the use of two lipases, as each lipase alone resulted in only partial splitting, [Park, Y. K., G. M. Pastore and M. M. deAlmeida, *J. Am. Oil Chem. Soc.*, 65:252–254, (1988)].

It has been reported that some enzymes retain their activity in organic solvents [Zaks, A., and A. M. Klibanov, *Proceedings of the National Academy of Sciences*, 82:3192–3196 (1985)]. Non-immobilized lipases from *Candida rugosa*, *Rhizomucor miehei* and porcine pancreas were shown to be catalytically active in organic solvents containing a trace of water for aminolysis, oximolysis and various esterification reactions. However, these enzyme systems were neither shown nor taught to be useful for hydrolytic reactions.

The use of lipases in non-aqueous solvents has been reviewed independently, by Gillis, A., *JAOCS*, 65:846–852 (1988); Klibanov, A. M., *TIBS*, 14:141–144 (1989); and Wong, C. H., *Science*, 244:1145–1152 (1989). In the majority of applications, these enzymes have been used to catalyze reactions such as the synthesis of ester bonds which are thermodynamically unfavorable in an aqueous medium. The lipase catalyzed formation of fatty amides from fatty acid methyl esters has also been reported, [Bistline, R. G., Jr., A. Bilyk, and S. H. Feairheller, *JAOCS*, 68:95–98 (1991)].

It has also been shown that lipases are lipolytically active in organic solvents. Use of fungal lipases in organic solvents, Bilyk et al., [*JAOCS*, 68:320–323, (1991)], achieved hydrolysis of a variety of fats and oils at moderate temperatures and in a relatively short time. Yield of fatty acids was limited to 76%, but with the addition of substantial amounts of substituted amines, yields of approximately 95% were obtained.

Lee and Hammond, in their article "Oat (*Avena sativa*) Caryopses as a Natural Lipase Bioreactor," *J. Am. Oil. Chem. Soc.*, 67:761–765, (1990), reported the initial rate of hydrolysis of coconut oil and castor oil relative to that of soybean oil, by whole, dehulled oat seeds. The reaction system consisted of caryopses wetted with water and immersed in a hexane and oil mixture. Sometimes the mixtures were gently stirred. Although it was possible to achieve up to 90% lipolysis, this required 58 days and three batches of oat seeds. Only a 10% conversion was achieved after 4 days. They postulated that the slow rate of hydrolysis may be due to inhibition of the enzyme by glycerol, a product of the reaction. This reference does not disclose a rapid method of oil or animal fat splitting. Nor does the reference disclose a method of recycling or regeneration of the enzymes.

In order to conserve energy and obtain light colored fatty acids, some companies have investigated industrial enzymatic fat splitting using processes which involve the mixing of fats with lipase, agitating for 2 to 4 days, and subsequently isolating the fatty acids and glycerol, [Meito Sangyo Col, Ltd., Jap. Pat. 79, 95, 607, *Chem. Abstracts*, 91, 21299069, (1979)]. For example, Miyoshi Fat and Oil, using a lipase supplied by Meito Sangyo Co., splits fats at 32° C., developed the capacity to produce 1000 metric tons of fatty acids per month. Meito Sangyo does not suggest or teach a rapid method of fat and oil splitting using a lipase catalyst found in seeds.

U.S. Pat. No. 5,032,515, "Hydrolysis Process of Fat or Oil," to Tanigake et al., is a method which describes the hydrolysis of fat or oil by the continuous or semi-continuous supplying of water and lipase while simultaneously withdrawing a solution containing the fatty acids and glycerol to maintain the glycerol concentration in a range of 10 to 40% by weight. Tanigake et al. use lipase from *Candida cylindracea*.

U.S. Pat. No. 4,865,978, Lipolytic Splitting of Fats and Oils, to Serota, uses a spiral heating/cooling coil and a special mixer having impeller blades and baffles to prevent mass swirling to enzymatically hydrolyze triglycerides.

A reduction in lipolytic reaction time and temperature would result in a substantial reduction in the fat inventories presently required for the production process and a concurrent decrease in energy consumption and cost. Since lipases are currently too expensive to only be used in a single batch process, the ability to reuse enzymes would enhance the attractiveness of enzymatic hydrolysis in an industrial setting.

SUMMARY OF THE INVENTION

The present invention relates to a new method of rapid lipolysis, by enzymatic hydrolysis of the triglycerides of oleaginous materials. Included in this group are oils such as cotton, soybean, corn, palm and castor oil, and fats such as tallow, lard, and butter. Reaction occurs in an organic solvent utilizing a lipase catalyst found in seeds. A high quality fatty acid and glycerol can be produced in a shortened period of time and with reduced energy requirements. No expensive lipase purification steps are required. The seeds are comminuted to activate the lipase which can optionally be recycled.

It has now been found that lipase catalysts recovered from pulverized seeds can rapidly split fats and oils of all types, regardless of their degree of saturation or hydroxylation. The process is performed in an organic solvent in the presence of water, at mild temperatures and using agitation. The rapid process resulting from this discovery reduces energy costs, facilitates recovery of the fatty acid product, and yields a product of superior quality, while remaining cost effective.

Lipase activity from whole oat seeds in a two phase oil-water system is dependent upon the presence of calcium ions. In the present invention, due to the reaction taking place in an organic solvent, calcium is not required.

The present invention provides a method for the rapid hydrolysis of oleaginous material at low temperature without the need of emulsifiers. The resultant fatty acids and glycerol can be readily recovered from the lipolysis reaction medium in the form of a substantially colorless and polymer-free product. Steps of product purification and distillation necessary in the prior art are not needed with the instant invention.

The present invention also eliminates the need for two process steps heretofor requisite in the use of lipase on an industrial scale: lipase purification and its immobilization on a support.

In the present invention the lipase catalyst can be recycled for use in multiple passes. Second pass reaction efficiencies of 90% have been achieved. The ability to recycle results in a substantial reduction in production costs. In this new method, the retail cost of oat seeds required to break down one pound of oil, assuming no recycling, is 23 cents. The retail cost of a commercial, immobilized lipase necessary to carry out the same function is $35.58, assuming no recycling.

Figure 1:
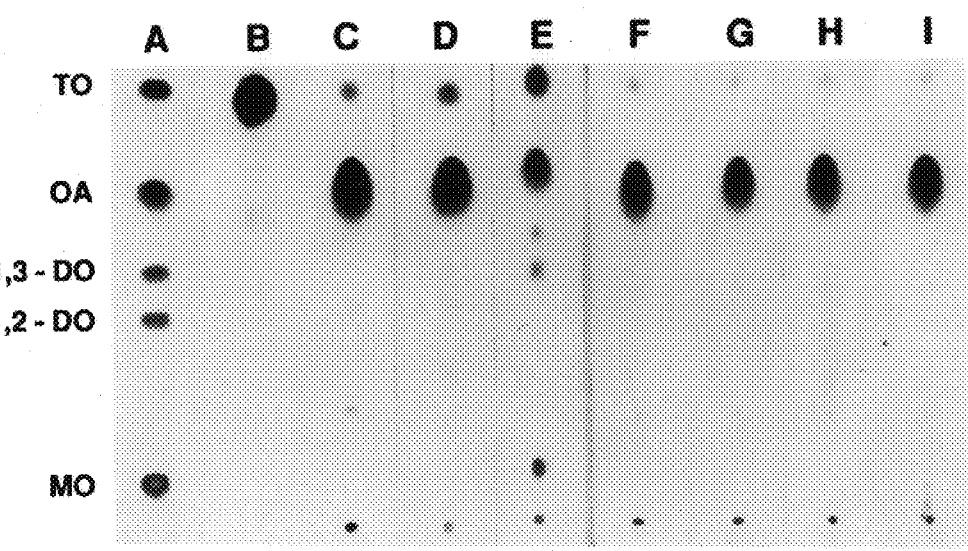
FIG. 1 is a thin-layer chromatography (TLC) analysis of the lipolysis of cotton, olive, soybean and corn oils by the lipase in ground oat seeds.

The above and additional objects, characteristics, and advantages of the present invention will become apparent in the following detailed description of preferred embodiments, with reference to the accompanying non-limiting examples.

DESCRIPTION OF THE PREFERRED EMBODIMENTS

It has been found that comminuted lipase-containing seeds, including oats and rice, can be used without further processing as an immobilized lipase for the hydrolytic splitting of oleaginous materials such as oils and fats derived from plants and animals into their constituent fatty acids and glycerol. Oleaginous materials are treated with this lipase source under reaction conditions which promote their essentially complete (more than about 97%) hydrolysis. Rapid reaction rates are obtained even under ambient conditions of temperature and pressure.

The lipase activity of the seeds is activated by comminution such as grinding, crushing, or pulverization. The endogenous lipids present in the seeds may optionally be removed by washing in an organic solvent. Lipase, being insoluble in such, remains affixed to the ground seeds. This simplified method distinguishes itself from conventional enzyme extraction techniques wherein the enzyme has heretofor first been purified and then subsequently immobilized on a solid support to facilitate its post-reaction recovery. In the present invention such steps are unnecessary as the ground seeds are utilized as the support structure. The comminuted lipase-containing seeds are then combined with an oleaginous material, an organic solvent, and sufficient water to promote triglyceride hydrolysis; and then agitated during reaction. It is not necessary for the oleaginous material to be completely soluble in the organic solvent: It was surprisingly found that nearly complete hydrolysis can be obtained without having the oleaginous material completely dissolved. Upon completion of the reaction, the liquid portion of the mixture containing the fatty acids is separated and the solid phase containing the lipase catalyst is recycled.

It is an essential element of the present invention that the oat or other seeds serving as the lipase source be prepared by comminution to make the lipase enzyme available. It is preferable that the entire seed, including the hull, be utilized. The endogenous glycerides and lipids of such seeds may optionally be extracted by use of an organic solvent prior to lipolysis of the oleaginous material. Usable solvents for this extraction include linear, branched and cyclic hydrocarbons containing from about 5 to about 12 carbon atoms. These compounds may be of one or more degrees of unsaturation and may be optionally substituted with one or more halo, hydroxy, ester, and ether functionalities. Supercritical gases such as carbon dioxide may also be used. The preferred solvents for extraction are 2,2,4-trimethylpentane (TMP) and diethyl ether. The extraction may be performed over a temperature range of about −20° C. to about 120° C. or the boiling point of the particular solvent, whichever is lowest. A preferred temperature range for extraction is from about 20° C. to about 30° C. The time for extraction may range from about 1 minute to about 48 hours. The preferred time for extraction is from about 10 minutes to about 1 hour, with about 30 minutes being most preferred.

Extraction of endogenous seed lipids is necessary only if an analysis of fatty acid release from the oleaginous substrate is to be performed using thin-layer chromatography. Defatting is not necessary in large scale commercial applications, as the endogenous seed lipids themselves are split by the lipase along with the treated oleaginous material and contribute to the overall production of fatty acids.

The hydrolytic production of fatty acids is carried out by first combining the oleaginous material with an organic solvent, water, and the comminuted lipase-containing seeds. Buffers and emulsifiers may optionally be added to the reaction mixture but are not required. The oleaginous material may be one or more of any source of mono, di and/or triglycerides, including oils such as cotton, soybean, corn, palm, castor and fish oils, and fats such as tallow, lard and butter. Usable solvents are any which promote the hydrolysis of the oleaginous material in the reaction mixture and include linear, branched and cyclic hydrocarbons containing from about 5 to about 12 carbon atoms. These compounds may be of one or more degrees of unsaturation and may be optionally substituted with one or more halo or ether functionalities. Supercritical gases such as carbon dioxide may also be used. The preferred solvents for hydrolysis are heptane, hexane and 2,2,4-trimethylpentane. The lipase-containing seeds may be any which possess lipase, with oat and rice being preferred, and oat being most preferred.

The preferred range of usable proportions for the components comprising the hydrolytic reaction mixture, based on the weight of the solvent component, are: about 0.50 to about 60 wt % water, about 0.50 to about 100 wt % oleaginous material, and about 0.50 to about 100 wt % non-defatted seeds; with individually most preferred ranges of about 2.5 to about 10 wt % water, about 0.50 to about 4 wt % oleaginous material and about 10 to about 33 wt % non-defatted seeds.

The hydrolytic reaction may be performed over a temperature range of about −20° C. to about 120° C. or the boiling point of the solvent, whichever is lowest. A preferred temperature range for hydrolysis is from about 10° C. to about 70° C. with a range from about 25° C. to about 45° C. being most preferred. The time for hydrolysis may range from about 1 hour to about 500 hours, with a preferred range of from about 3 hours to about 36 hours. The mixture is agitated at a speed which is sufficient to promote the reaction by mixture of the liquid and solid phases, with a range of from about 50 rpm to about 500 rmp being preferred and a speed of about 200 rpm being most preferred. While ambient pressure is preferred the reaction may be operated at pressures either higher or lower as long as the phases of the reaction mixture are not subjected to a change of state. The process may be operated in a batch, continuous or semi-continuous mode as desired.

The fatty acids and glycerol may be recovered from the reaction mixture simply by decanting the solvent from the comminuted seed particles. However, since not all fatty acids are completely soluble in nonpolar solvents, an additional wash with another solvent may sometimes be used to maximize yield. For example, the fatty acids contained in castor oil are slightly polar due to their hydroxylation and are therefor more amenable to solvation and subsequent extraction by a polar compound such as diethylether. The glycerol may be separated from the fatty acids through conventional procedures such as extraction with water.

The lipase utilized in the instant invention functions with no measurable selectivity regarding fatty acids. All fatty acids, regardless of their identity, are split from the glyceride with the fatty acid composition of the resultant product being solely dependent on the oleaginous material used as the source. For example, when tallow is hydrolyzed approximately 50% of the fatty acids produced are saturated and 50% are mono-unsaturated. When soybean oil is used 50% of the fatty acids are polyunsaturated. When castor oil is used approximately 90% of the fatty acids produced are hydroxylated.

The present invention possesses substantial advantages over the existing processes of enzymatic fat hydrolysis. The addition of a buffer or an emulsifier to the reaction mixture, and adjustment of the pH, are not necessary. When fat splitting is conducted in the aqueous medium of the prior art, the pH of the medium must be held as constant as possible, with the fatty acids, upon their release, being converted into insoluble salts. These salts usually form a clump in which incompletely hydrolyzed glycerides are trapped. As a result, it is usually not possible to achieve more than 80% of the theoretical maximum hydrolysis unless some sort of mixing is used to continuously break up the precipitated clumps of the fatty acid salts. Likewise when lipolysis is conducted in an aqueous emulsion of the existing art, recovery of the fatty acids requires acidification prior to extraction with an organic solvent. The present invention, in producing the fatty acids in the non-salt form, does not require acidification.

The comminuted seed particles, retaining lipase therein, may be recovered from the reaction mixture for recycling. Optimal activity is achieved by first drying and regrinding the seed particles prior to their reuse.

EXAMPLE 1

Lipase Preparation. Oat seeds (4 g) were ground in a 37 ml Waring mini jar for 15 seconds. Endogenous oil lipids were extracted by stirring the ground oats twice with 75 ml diethylether for 30 minutes at room temperature. The diethylether was decanted, and residual solvent was removed by placing the oats in a vacuum desiccator.

Lipolysis of Soybean Oil in an Organic Solvent. All reactions were conducted in 125 ml Erlenmeyer flasks equipped with glass stoppers. Hydrolysis in an organic solvent was conducted as follows: defatted oats (4 g before defatting) were added to a mixture of 0.4 g of soybean oil, 16 ml of 2,2,4-trimethylpentane and 0.8 ml of water. The flask was shaken in a Controlled Environment Incubator Shaker (New Brunswick Scientific, New Brunswick, N.J.) at 200 rpm.

Lipolysis of Soybean Oil in an Aqueous Medium. Aqueous lipolysis was conducted to demonstrate that only incomplete splitting can be obtained in an aqueous medium (FIG. 1, Lane E). Aqueous hydrolysis was conducted as follows: soybean oil (0.4 g), 10% gum arabic (8 ml), and 2M tricine (8 ml) were placed in the flask (final pH 9.0), and the mixture was sonicated to achieve a uniform emulsion. After the addition of defatted oats (4 g before defatting), the flask was shaken in a Controlled Environment Incubator Shaker (New Brunswick Scientific, New Brunswick, N.J.) at 200 rpm.

Analysis of Lipolysis Products. In contrast to the preparation for analysis of fatty acids derived from an aqueous medium, the fatty acid products generated in organic solvent can be analyzed by thin-layer chromatography (TLC) without prior treatment.

In the aqueous medium, the following steps were taken: the pH of the reaction solution was first lowered to pH 3.0 by the addition of concentrated sulfuric acid. Then the fatty acids were extracted with organic solvent. The TLC plates were developed and visualized, and gas-liquid chromatography (GLC) of the fatty acid fraction was conducted.

Figure 2:
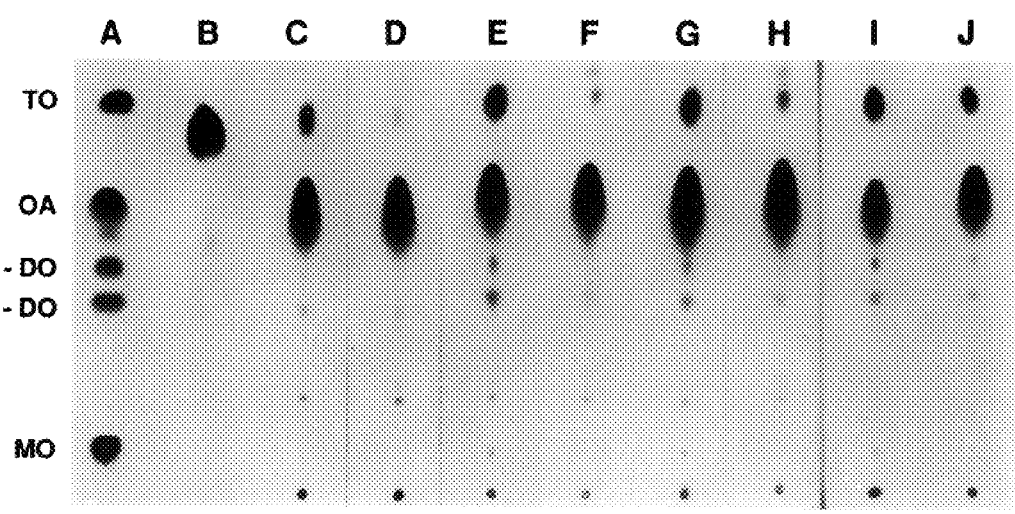
FIG. 2 is a TLC analysis of the lipolysis of soybean oil using the lipase derived from ground oat seeds. The reaction takes place in the organic solvent trimethylpentane (TMP) at various temperatures.

An analysis of the results achieved in EXAMPLE I, are shown in FIGS. 1 and 2.

FIG. 1 is a TLC analysis of the lipolysis of cotton, olive, soybean and corn oils. Lipolysis is achieved with the lipase derived from ground oats with the reaction at 24° C. FIG. 1 illustrates nine lanes, A–I, with lane A consisting of the standards triolein (TO), oleic acid (OA), 1,3-diolein (1,3-DO), 1,2-diolein (1,2-DO) and monolein (MO). Lane B illustrates unreacted soybean oil. Lane C exhibits the results of incubating soybean oil with comminuted oat seeds in TMP over a 24 hour reaction time. Lane D is the same as Lane C, except that 1.38 g of sulfuric acid and 6.4 ml of isopropanol were added to the reaction medium and shaken for one minute. Lane E exhibits the results of incubating soybean oil with comminuted oat seeds in an aqueous-gum arabic emulsion over a 24 hour reaction time. Lanes F,G,H and I illustrate the results of incubating cotton, olive, soybean and corn oils, respectively, with comminuted oat seeds in TMP over a 48 hour reaction time.

FIG. 2 is a TLC analysis of the lipolysis of soybean oil by the lipase derived from ground oat seeds in TMP at various temperatures under the reaction conditions in the description regarding FIG. 1 above. There are ten lanes illustrated in FIG. 2, A–J. Lanes A and B contain the same standards as in FIG. 1. In lane C, the reaction time is 6 hours at 35° C.; lane D, 19 hours at 35° C.; lane E, 6 hours at 45° C.; lane F, 19 hours at 45° C.; lane G, 6 hours at 55° C.; lane H, 19 hours at 55° C.; lane I, 6 hours at 65° C.; and lane J, 19 hours at 65° C.

EXAMPLE II

Lipase Preparation, Oat seeds (4 g) were ground in a 37 ml Waring mini jar for 15 seconds. Endogenous oat lipids were extracted by stirring the ground oats twice with 75 ml diethylether for 30 minutes at room temperature. The diethylether was decanted, and the residual solvent was removed by placing the oats in a vacuum desiccator.

Lipolysis of Castor Oil in an Organic Solvent. All reactions were conducted in 125 ml Erlenmeyer flasks equipped with a glass stopper. Hydrolysis in an organic solvent was conducted as follows: defatted oats (4 g before defatting) was added to a mixture of 0.4 g of castor oil, 16 ml of 2,2,4-trimethylpentane and 0.8 ml of water. The flask was shaken in a Controlled Environment Incubator Shaker (New Brunswick Scientific, New Brunswick, N.J.) at 200 rpm.

Analysis of Lipolysis Products. The fatty acids generated in organic solvent can be analyzed by thin-layer chromatography (TLC) without prior treatment.

An analysis of the results achieved in EXAMPLE II as determined by the titration method of Linfield et. al. [Linfield, W. M., R. A. Barawskas, L. Sivieri, S. Serota and R. W. Stevenson, Sr., *J. Am. Oil Chem. Soc.*, 61:1067–1071 (1984)], is shown in Tables 1, 2 and 3.

Table 1 shows the effect of the castor oil level upon the amount of fatty acid released in one hour at 35° C. by the lipase in oat seeds.

TABLE 1

| Amount of Castor Oil g | Amount of trimethylpentane g | Castor Oil % | Fatty Acid Released μmol | Fatty Acid Released % |
|---|---|---|---|---|
| 0.4 | 15.6 | 2.5 | 328 | 25.2 |
| 1.0 | 15.0 | 6.25 | 343 | 10.6 |
| 2.0 | 14.0 | 12.5 | 386 | 5.9 |
| 4.0 | 12.0 | 25.0 | 412 | 3.2 |
| 8.0 | 8.0 | 50.0 | 635 | 2.4 |
| 12.0 | 4.0 | 75.0 | 378 | 0.97 |
| 16.0 | 0.0 | 100.0 | 44 | 0.085 |

Table 2 shows the time course of fatty acid released at 35° C. by the lipase in oat seeds when the level of castor oil is low (oil:oil+TMP; 0.4:16 w/w).

TABLE 2

| Time h | Fatty Acid Released μmol | Fatty Acid Released % |
|---|---|---|
| 0.5 | 165 | 12.7 |
| 1 | 406 | 31.3 |
| 1.5 | 519 | 40.0 |
| 2.5 | 752 | 57.9 |
| 3.5 | 994 | 76.6 |
| 7.5 | 1216 | 93.6 |
| 22.5 | 1281 | 98.7 |

Table 3 shows the time course of fatty acid released at 35° C. by the lipase in oat seeds when the level of castor oil is high (oil:oil+TMP; 8:16 w/w/).

TABLE 3

| Time h | Fatty Acid Released μmol | Fatty Acid Released % |
|---|---|---|
| 1.5 | 1.34 | 5.2 |
| 3 | 3.13 | 12.1 |
| 6 | 4.77 | 18.4 |
| 12 | 7.69 | 29.6 |
| 24 | 11.45 | 44.1 |
| 54 | 15.10 | 58.2 |
| 102 | 19.56 | 75.3 |
| 216 | 19.94 | 76.8 |
| 311 | 23.07 | 88.8 |

EXAMPLE III

Lipase Preparation. Oat seeds (4 g) were ground in a 37 ml Waring mini jar for 15 seconds. Endogenous oat lipids were extracted by stirring the ground oats twice with 75 ml diethylether for 30 minutes at room temperature. The diethylether was decanted, and the residual solvent was removed by placing the oats in a vacuum desiccator.

Lipolysis of Palm Oil, Tallow, Lard, and Butter Fat in an Organic Solvent. All reactions were conducted in 125 ml Erlenmeyer flasks equipped with a glass stopper. Hydrolysis in an organic solvent was conducted as follows: defatted oats (4 g before defatting) was added to a mixture of 0.4 g of either palm oil, tallow, lard, or butter fat, 16 ml of 2,2,4-trimethylpentane and 0.8 ml of water. The flask was shaken in a Controlled Environment Incubator Shaker (New Brunswick Scientific, New Brunswick, N.J.) at 200 rpm.

Analysis of Lipolysis Products. In contrast to the preparation for analysis of fatty acids derived from an aqueous medium, the fatty acid products generated in organic solvent can be analyzed by thin-layer chromatography (TLC) without prior treatment.

In the aqueous medium, the following steps would be taken: the pH of the reaction solution would first be lowered to pH 3.0 by the addition of concentrated sulfuric acid. Then the fatty acids would be extracted with organic solvent. The TLC plates would be developed and visualized, and gas-liquid chromatography (GLC) of the fatty acid fraction would be conducted.

Figure 3:
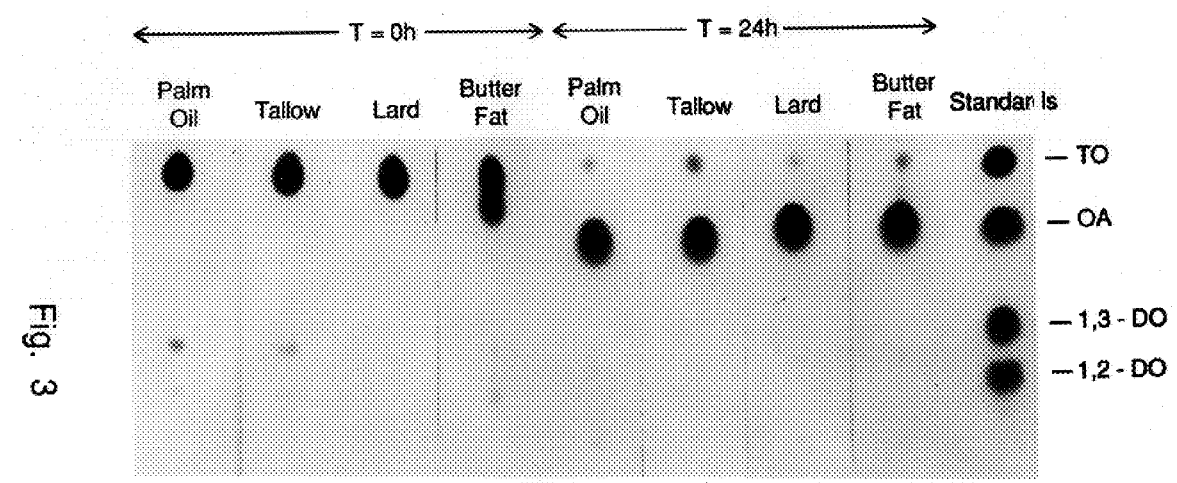
FIG. 3 shows the products resulting from the splitting of palm oil, tallow, lard, and butter fat by the lipase in oat seeds at 35° C. for 24 hours.

An analysis of the results achieved in EXAMPLE III, is shown in FIG. 3.

FIG. 3 illustrates the splitting of palm oil, tallow, lard, and butter fat by the lipase of oat seeds at 35° C. for 24 hours. The lanes are as shown on the figure. The standards consist of triolein (TO), oleic acid (OA), 1,3-diolein (1,3-DO), 1,2-diolein (1,2-DO) and monolein (MO).

Finally, although the invention has been described with reference of particular means, materials and embodiments, it is to be understood that the invention is not limited to the particulars disclosed and extends to all equivalents within the scope of the claims.

We claim:

1. A method of producing fatty acids and glycerol by the hydrolysis of oleaginous materials, utilizing an immobilized lipase in the form of comminuted lipase-containing seeds, comprising the steps of:
   a. comminuting the seeds to form an immobilized lipase;
   b. mixing an organic solvent, water and an oleaginous material with the immobilized lipase to form a reaction medium;
   c. agitating the reaction medium under conditions effective to hydrolyze said oleaginous material; and
   d. separating the fatty acids and glycerol from the reaction medium.

2. The method of claim 1 wherein the comminuted seeds are oats.

3. The method of claim 1 wherein the comminuted seeds are rice.

4. The method of claim 1 wherein the degree of hydrolysis is at least about 97%.

5. The method of claim 1 including the further step of extracting the endogenous lipids from the comminuted seeds prior to formation of a reaction medium.

6. The method of claim 1 wherein the reaction is carried out in a batch, continuous or semi-continous process.

7. The method of claim 1 including the further step of separating the glycerol from the fatty acids.

8. The method of claim 7 wherein said separation is by extraction with water.

* * * * *